(12) United States Patent
Selkee (10) Patent No.: US 8,298,177 B2
(45) Date of Patent: Oct. 30, 2012

(54) INSERT MOLDED CATHETER PULLER MEMBER CONNECTORS AND METHOD OF MAKING THE SAME

(75) Inventor: Thomas V. Selkee, Claremont, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 364 days.

(21) Appl. No.: 12/564,333

(22) Filed: Sep. 22, 2009

(65) Prior Publication Data

US 2010/0164137 A1 Jul. 1, 2010

Related U.S. Application Data

(62) Division of application No. 11/555,059, filed on Oct. 31, 2006, now Pat. No. 7,931,616.

(51) Int. Cl.
*A61M 31/00* (2006.01)

(52) U.S. Cl. .................................. 604/95.01

(58) Field of Classification Search ............... 604/95.01
See application file for complete search history.

(56) References Cited

U.S. PATENT DOCUMENTS

| | | | |
|---|---|---|---|
| 4,996,974 A * | 3/1991 | Ciarlei | 600/149 |
| 5,167,221 A | 12/1992 | Chikama | |
| 5,395,327 A | 3/1995 | Lundquist et al. | |
| 5,741,320 A | 4/1998 | Thornton et al. | |
| 5,891,088 A * | 4/1999 | Thompson et al. | 604/95.04 |
| 5,904,667 A | 5/1999 | Falwell | |
| 5,944,690 A | 8/1999 | Falwell et al. | |
| 6,033,378 A | 3/2000 | Lundquist et al. | |
| 6,120,476 A | 9/2000 | Fung et al. | |
| 6,210,407 B1 * | 4/2001 | Webster | 606/41 |
| 6,508,789 B1 * | 1/2003 | Sinnott et al. | 604/164.02 |
| 6,579,278 B1 | 6/2003 | Bencini | |
| 6,602,242 B1 | 8/2003 | Fung et al. | |
| 6,648,875 B2 | 11/2003 | Simpson et al. | |
| 6,702,737 B2 * | 3/2004 | Hino et al. | 600/146 |
| 7,377,906 B2 | 5/2008 | Selkee | |
| 7,591,799 B2 | 9/2009 | Selkee | |

(Continued)

FOREIGN PATENT DOCUMENTS

EP 0790066 B1 4/2000

OTHER PUBLICATIONS

Microplastics Inc, http://www.microplasticsinc.com/what_is_insert_molding.php.*

*Primary Examiner* — Nicholas Lucchesi
*Assistant Examiner* — Diva K Chander
(74) *Attorney, Agent, or Firm* — William A. Schoneman

(57) ABSTRACT

The present invention is directed to a method of securing a puller member in a control handle for a deflectable catheter. The method comprises preforming an end of the puller member, placing the preformed end in an insert mold, filling the insert mold with thermoplastic material to form a molded member, and positioning the molded member encasing the end of the puller member in a control handle.

The method may also include shaping the thermoplastic material into a screw configuration and fastening the molded member to a wall in the control handle. The method may further include joining the end of the puller member with an end of a second puller member, and placing joined ends of the puller members in the insert mold.

9 Claims, 8 Drawing Sheets

U.S. PATENT DOCUMENTS

| | | |
|---|---|---|
| 7,931,616 B2 * | 4/2011 | Selkee ............... 604/95.04 |
| 8,137,308 B2 * | 3/2012 | Schultz ............... 604/95.04 |
| 2004/0143197 A1 | 7/2004 | Soukup et al. |
| 2005/0149159 A1 | 7/2005 | Andreas et al. |
| 2005/0277874 A1 | 12/2005 | Selkee |
| 2005/0277875 A1 * | 12/2005 | Selkee ............... 604/95.04 |
| 2006/0141595 A1 | 6/2006 | Prabhune et al. |
| 2006/0142695 A1 | 6/2006 | Knudson |
| 2006/0189978 A1 | 8/2006 | Smith |
| 2006/0258979 A1 | 11/2006 | Fischer et al. |
| 2006/0270975 A1 | 11/2006 | Savage |
| 2006/0270976 A1 | 11/2006 | Savage et al. |
| 2007/0156133 A1 | 7/2007 | McDaniel et al. |
| 2008/0255540 A1 | 10/2008 | Selkee |
| 2009/0182269 A1 | 7/2009 | Selkee |

* cited by examiner

INSERT MOLDED CATHETER PULLER MEMBER CONNECTORS AND METHOD OF MAKING THE SAME

CROSS REFERENCE TO RELATED APPLICATION

This application is a Divisional of prior application Ser. No. 11/555,059, filed Oct. 31, 2006, now U.S. Pat. No. 7,931,616 and claims priority to such under 35 USC §121.

FIELD OF INVENTION

The present invention relates to deflectable catheters, and more particularly to method of making catheters with tensile members to effectuate deflection.

BACKGROUND OF INVENTION

Electrode catheters have been in common use in medical practice for many years. They are used to stimulate and map electrical activity in the heart and to ablate sites of aberrant electrical activity. In use, the electrode catheter is inserted into a major vein or artery, e.g., femoral artery, and then guided into the chamber of the heart which is of concern. Within the heart, the ability to control the exact position and orientation of the catheter tip is critical and largely determines how useful the catheter is.

Deflectable catheters have been designed to provide deflection in at least one direction by a puller wire, if not also deflection in an opposite direction by a second puller wire. In such a construction, the puller wires extend into opposing off-axis lumens within a distal section of the catheter. For example, U.S. Pat. No. 6,210,407, the disclosure of which is incorporated herein by reference, is directed to a bi-directional catheter comprising two puller wires and a control handle having at least two moveable members longitudinally movable between first and second positions. The proximal end of each puller wire is connected to an associated movable member of the control handle. Proximal movement of a movable member relative to the catheter body results in proximal movement of the puller wire associated with that movable member relative to the catheter body, and thus deflection of the tip section in the direction of the lumen in which that puller wire extends.

While the aforementioned catheter provides bi-directional steering, the mechanical efficiencies of the steering and the deflection mechanism of the control handle can be improved upon. For example, the use of pulleys in the control handle can increase the throw capacity of the catheter. However, the repeated bending and straightening of the puller wires trained around the pulleys during deflection operations can significantly reduce the life span of the puller wires due to fatigue failure. If a different tensile material is trained around the pulleys, means for connecting this different material to a puller wire can pose additional challenges.

Current means for attaching puller wire ends typically involve mechanical crimping utilizing a stainless steel ferrule crimped on the puller wire end. The stainless to stainless steel crimping process may cause puller wire surface deformation (nicks or notches) that change the wire section modulus thus creating localized stress raisers that have a propensity to initiate crack propagation during puller wire tensile force cycling that occurs during catheter handle actuation. Due to limited space in the catheter shaft, the puller wire is designed to be as small as possible thus it is subjected to high tensile stresses during catheter handle operation. Any changes in the puller wire's cross sectional area in tension could result in puller wire failure during catheter operation. Hence, there is a desire for a deflectable catheter whose puller wire connections avoid such surface deformations.

SUMMARY OF THE INVENTION

The present invention provides a deflectable catheter whose puller member connections are accomplished with minimal, if any, surface deformation which could otherwise accelerate breakage under tension. The deflectable catheter comprises an elongated catheter body, a deflectable section distal the catheter body, a control handle proximal the catheter body, and a puller member responsive to the control handle to deflect the deflectable section. Advantageously, the catheter includes a molded member that encases an end of the puller member to enable connection of the end to a fixed or movable structure in the control handle, such as a wall for anchoring, a spring for tension adjustment, or even to another puller member, without any surface deformation or cross sectional area changes in the puller member. In accordance with a feature of the present invention, the molded member consists of a thermoplastic material that encases a preformed end of the puller member, which may be a puller wire or a high modulus (resistance to creep under load) and tensile strength fiber material.

To better hold the end of the puller member in the molded member, the end of the puller member is preformed with a knot, a loop or a coil. The molded member may be configured as desired, for example, as a screw that is fastened to a structure in the control handle as a means to anchor the puller member to the control handle. Alternatively, the preformed end of the puller member, for example, a puller wire, can be directly connected to and jointly encased in the molded member with another preformed end of a second puller member, for example, a high modulus fiber material. Such a connected puller member whose distal portion is the puller wire and whose proximal portion is the high modulus fiber material can be well suited for control handle that employs pulleys for increased throw capacity. In one embodiment, the connected puller member is positioned in the control handle while the distal puller wire extends distally from the control handle. As such, it is the proximal high modulus fiber material, and not the puller wire, that interacts with the deflection mechanism and bears the repetitions of bending and straightening around a pulley during catheter handle deflection operations.

In a more detailed embodiment, the molded member is translucent or transparent so that the encased end(s) can be inspected. It is also contemplated that the molded member be visible through a window provided in the control handle housing, as a visual indication of deflection and degree of deflection. To that end, the molded member can bear indicia and/or contain phosphors so that the movement and position of the molded member within the control handle can be readily assessed by a user in low ambient light. In yet another detailed embodiment, the control handle housing is configured with a track along which the molded member moves during deflection for quieter and smoother operation.

The present invention is also directed to a method of securing a puller member in a control handle for a deflectable catheter, comprising preforming an end of the puller member, placing the preformed end in an insert mold, filling the insert mold with thermoplastic material to form a molded member, and positioning the molded member encasing the end of the puller member in a control handle.

The method may also include shaping the thermoplastic material into a screw configuration and fastening the molded member to a wall in the control handle. The method may further include joining the end of the puller member with an end of a second puller member, and placing joined ends of the puller members in the insert mold.

In an embodiment, a joined connection between two puller members comprises a loop formed in the end of one puller member, and a knot formed in the end of the other puller member, wherein the one puller member is a puller wire and the other puller member is a high modulus fiber material. Alternatively, the joined connection comprises a coil formed in the end of one puller member, and a knot formed in the end of the other puller member, wherein the one puller member is a puller wire and the other puller member is a high modulus fiber material.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
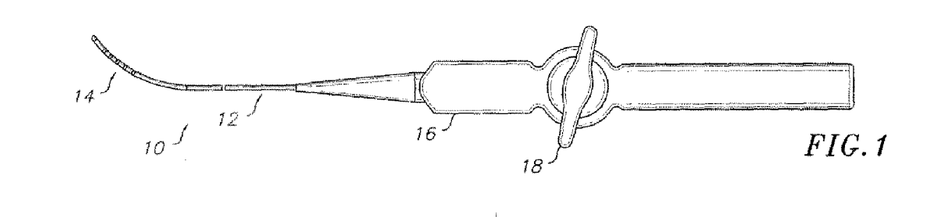
FIG. 1 is a side view of an embodiment of the catheter of the invention.

The present invention provides deflectable catheter puller wire joint connections and terminations with improved durability against material fatigue and breakage due to stresses borne during deflection operations. As shown in FIG. 1, the catheter 10 comprises an elongated catheter body 12 having proximal and distal ends, a deflectable section 14 distal the catheter body 12, and a control handle 16 at the proximal end of the catheter body 12. Description of suitable construction of the catheter body 12 and the deflectable section 14 can be found in U.S. Pat. Nos. 6,602,242 and 6,120,476, the entire disclosures of which are hereby incorporated by reference.

For deflecting the deflectable section 14, the catheter 10 has puller members 32 that extend from the control handle through the catheter body 12 to the deflectable section 14. Distal ends of the puller members 32 are anchored in the deflectable section 14 and their proximal ends are anchored in the control handle. Longitudinal movement of the puller members 32 relative to the catheter body 12, which results in deflection of the tip section 14, is accomplished by manipulation of a deflection knob 18 on the control handle 16. A suitable bidirectional control handle is generally described in U.S. application Ser. No. 10/871,691, filed Jun. 15, 2004, the entire disclosure of which is hereby incorporated by reference.

Figure 1A:
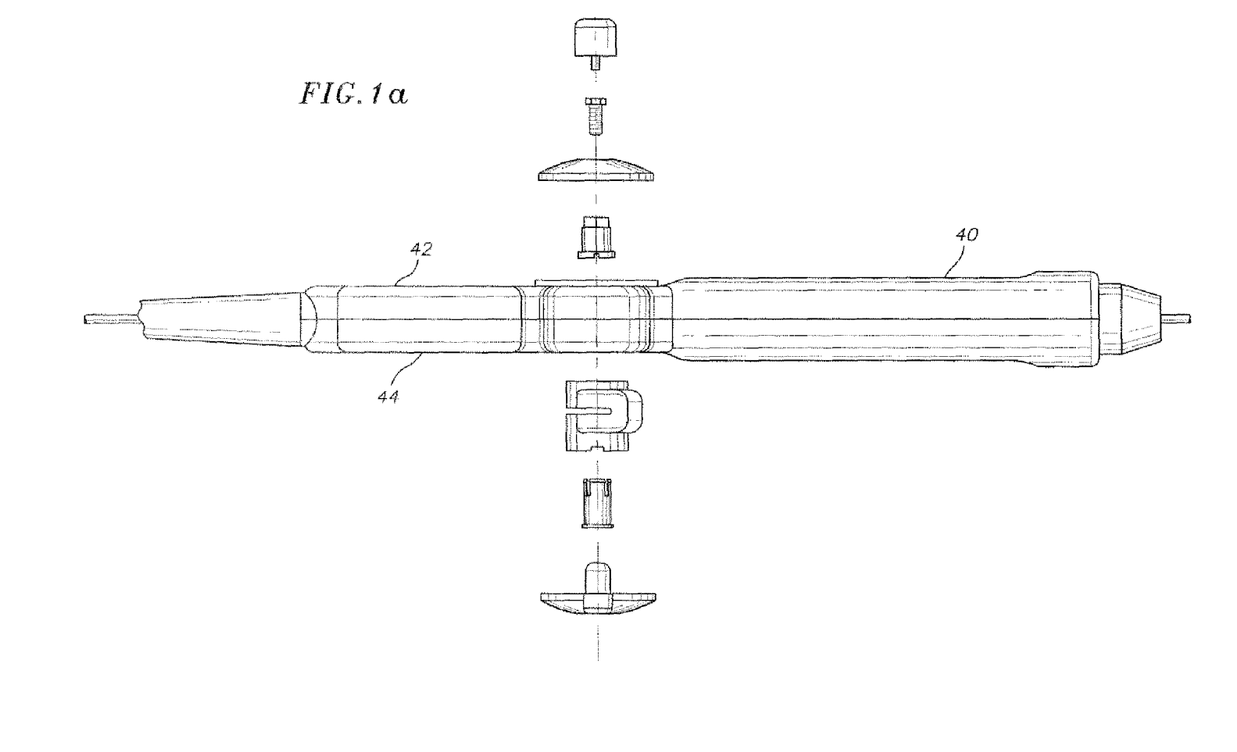
FIG. 1a is an exploded top view of a control handle of the catheter of FIG. 1.
Figure 2:
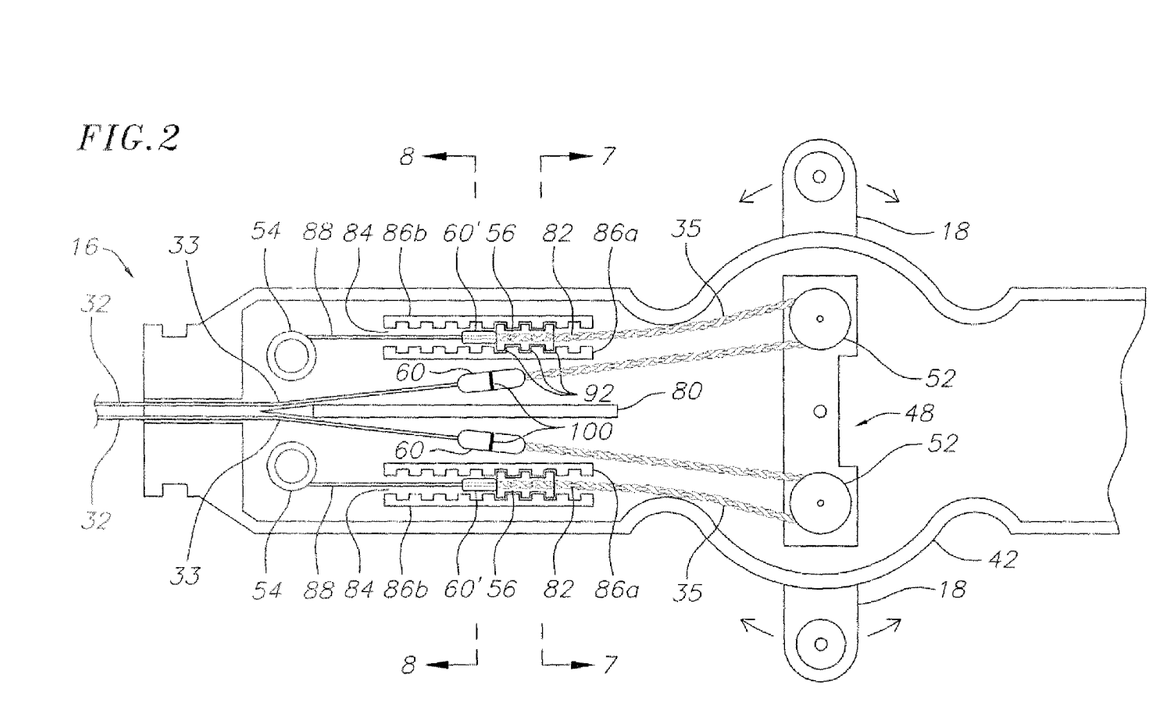
FIG. 2 is a top plan view of an embodiment of a deflection assembly within a housing half of a control handle.

With reference to FIG. 1a, the control handle 16 comprises a generally elongated handle housing 40, which can be made of any suitable rigid material. In the illustrated embodiment, the housing 40 has two opposing halves 42, 44 that are joined by glue, sonic welding or other suitable means. The control handle 16 employs means for deflection that is responsive to an operator in deflecting the catheter. With reference to FIG. 2, the illustrated embodiment of the control handle 16 employs a steering or deflection assembly 48 having a lever structure 50 carrying a pair of coordinated pulleys 52 that act on the puller members 32 to deflect the section 14. The deflection knob 18 and the lever structure 50 are rotationally coupled such that rotation of the deflection knob by a user rotates the lever structure which draws the puller members 32 to deflect the distal section 14. There are also a pair of stops 56 that help effectuate deflection by applying tension on the puller elements, and a pair of constant force springs 54 attached to the proximal ends of the puller members to take up slack. As described below in further detail, the placement of the stops 56 is adjustable to vary the tension on the puller members.

The control handle 16 is configured such that while the pulleys 52 of the steering assembly 48 increase the throw capacity of the catheter 10, the puller members are not exposed to an increased risk of fatigue or breakage attributable to the pulleys. In accordance with the present invention, each puller member 32 may be a connected or segmented puller member having multiple puller members that are joined in series. In the illustrated embodiment, the puller member 32 has a distal puller wire portion 33 and a proximal tensile fiber portion 35 such that the puller wire portion 33 extends from the control handle 16 to the deflectable section 14 and the proximal tensile fiber 35 engages the pulley within the control handle. In this manner, the more flexible tensile fiber portion 35 interacts with the pulley and it, as opposed to the puller wire 33, undergoes repeated bending and straightening during deflection operations. The tensile fibers 35 therefore saves the puller wires 33 from bending stress imposed fatigue failure caused by the pulleys 52.

Each puller wire portion or puller wire 33 is made of any suitable metal, such as stainless steel or Nitinol. Preferably each puller wire 33 has a low friction coating, such as a coating of Teflon® or the like. Each puller wire 33 has a diameter preferably ranging from about 0.006 inch to about 0.012 inch. Preferably both of the puller wires 33 have the same diameter.

Each tensile fiber portion or tensile fiber 35 may be of a high modulus fiber material, preferably having an ultimate tensile strength substantially in the range of 412-463 ksi (2480-3200 Mpa) such as High Molecular Density Polyethylene (e.g., Spectra™ or Dyneema™), a spun para-aramid fiber polymer (e.g., Kevlar™) or a melt spun liquid crystal polymer fiber rope (e.g., Vectran™), or a high strength ceramic fiber (e.g., Nextel™). The term fiber is used herein interchangeably with the term fibers in that the tensile fiber may be of a woven or braided construction. In any case, these materials tend to be flexible, providing suitable durability when used in wrapped engagement with the pulleys 52 and the like for greater throw in the control handle 16 for deflecting the catheter tip. Further, they are substantially non-stretching, which increases the responsiveness to the manipulation of the control handle, and nonmagnetic so that they generally appear transparent to an MRI. The low density of the material causes it to be generally transparent to an x-ray machine. The materials can also be nonconductive to avoid shorting. Vectran™, for example, has high strength, high abrasion resistance, is an electrical insulator, nonmagnetic, is polymeric, and has low elongation under sustained loading conditions.

In accordance with the present invention, the puller wire 33 and the tensile fiber 35 are connected or secured to each other by a molded member 60 that encases preformed/preshaped adjacent ends 63, 65 within a thermoplastic material that is formed by insert molding. Referring to FIGS. 3-6, the molded member 60 provides an advantageously small interconnection volume for a space-limited control handle, that secures the puller wire 33 and the tensile fiber 35 to each other and the thermoplastic material is generally self-dampening so there is little if any perceptible noise generated in the control handle during catheter deflection. Moreover, the thermoplastic material can be translucent, if not transparent, allowing passage of light, so that after formation of the molded member 60 the adjacent ends 63, 65 and interior of the molded member 60 can be visibly inspected. Significantly, the molded member 60 allows the puller wire 33 and the tensile member 35 to be connected in a manner that minimizes deformations or changes in cross-sectional area of the puller wire end 63 that can create localized stress raisers that are attributed to breakage and deflection failure. It is understood by one of ordinary skill in the art that the preshaping of the puller wire ends can be a manual process and/or an automated process.

Figure 3:
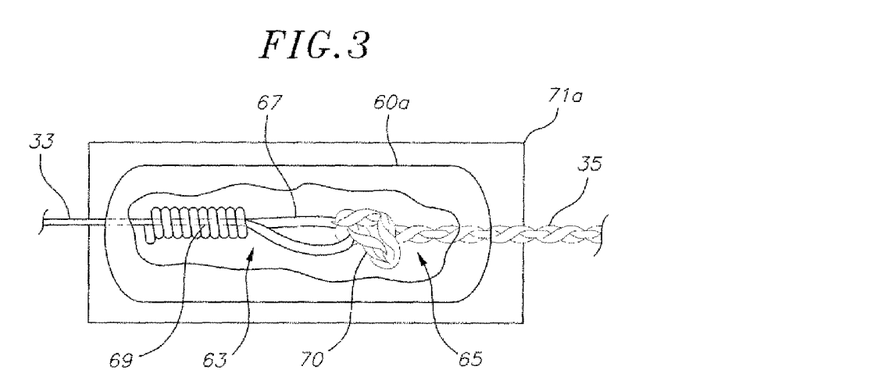
FIG. 3 is a side view of a first embodiment of a molded member securing two puller members to each other.

With reference to FIG. 3, an embodiment of a molded member 60a is shown as encasing interconnected preformed ends 63 of the puller wire 33 and 65 of the tensile fiber 35. The proximal end of the puller wire 33 is turned back on itself to form a loop 67 and wound about a more distal portion 69 that remains linear, with at least ten turns. The distal end of the tensile fiber 35 is inserted through the loop 67, turned back on itself and tied with a more distal portion to form a knot 70. The two ends are placed centrally in an insert mold 71a that is filled with thermoplastic material to encapsulate the joined two ends and portions distal and proximal thereof.

In this configuration, the puller wire 33 and the tensile fiber 35 are generally linearly aligned with each other and there is relatively low residual stress in the preformed end of the puller wire 33 that is subjected to alternative tensile forces. This embodiment can provide favorable tensile force versus elongation curves during cyclic tensile loading conditions at 500 cycles, which in turn can afford a connection with a greater average tensile force at breakage. Additionally, this embodiment of the molded member 60 can tolerate a smaller molded volume.

Figure 4:
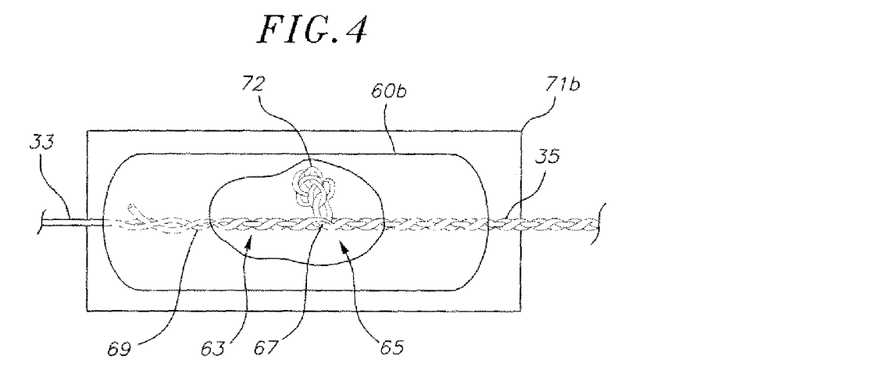
FIG. 4 is a side view of a second embodiment of a molded member securing two puller members to each other.

With reference to FIG. 4, another embodiment of a molded member 60b is shown as encasing interconnected preformed end of the puller wire 33 and the preformed end 65 of the tensile fiber 35. The proximal end of the puller wire is turned back on itself to form the loop 67 and twisted together with the more distal portion 69, with at least ten turns, preferably at least 12 turns. The distal end 65 of the tensile fiber 35 is inserted through the loop 67 and tied to form a knot 72 that is larger than the loop 67 and prevents the distal end 35 from slipping out of the loop. The two ends are placed centrally in an insert mold 71b that is filled with thermoplastic material to encapsulate the joined two ends and portions distal and proximal thereof.

In this configuration, the puller wire 33 may be subjected to a bending moment and tensile forces during deflection and thus have a lower tensile force at puller wire failure than the above embodiment of FIG. 3. Due to the greater number of turns in the puller wire 33, the molded member 60b may have a greater insert molded length than the molded member 60a. However, the molded member 60b still provides favorable tensile force versus elongation curves during cyclic tensile loading conditions at 500 cycles.

Figure 5:
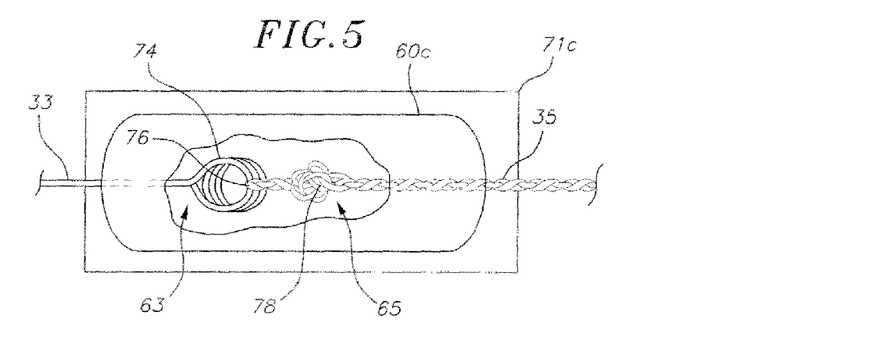
FIG. 5 is a side view of a third embodiment of a molded member securing two puller members to each other.

With reference to FIG. 5, yet another embodiment of a molded member 60c is shown as encasing interconnected preformed ends 63 and 65. The proximal end 63 of the puller wire 33 is shaped with a coil 74 with at least four windings to form a channel 76 through which the distal end 65 of the tensile fiber 35 is inserted, turned back and tied with a more distal portion of the tensile fiber to form a knot 78. The two ends are placed centrally in an insert mold 71c that is filled with thermoplastic material to encapsulate the joined two ends and portions distal and proximal thereof.

In this configuration, the puller wire 33 can be subjected to tensile and bending moment forces during cyclic tensile testing; thus, the force at puller wire failure can be lower than either of the aforementioned embodiments. The molded member 60c may provide less favorable tensile force versus elongation curves during cyclic tensile loading conditions when compared to the molded members 60a and 60b. Due to the size of the coil and number of windings, the molded member 60c can have a insert molded volume greater than the aforementioned embodiments.

Figure 6:
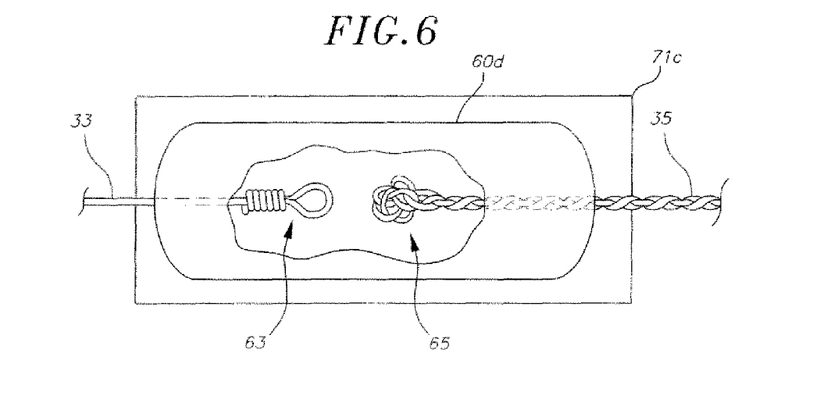
FIG. 6. is a side view of a fourth embodiment of a molded member securing two puller members to each other

With reference to FIG. 6, a further embodiment of a molded member 60d is shown as encasing adjacent but free preformed ends 63 and 65. The end 63 and 65 can be preformed in any of the aforementioned manners, and the puller wire 33 and tensile fiber 35 are in linear alignment with each other. The two ends are placed centrally in an insert mold 71d that is filled with thermoplastic material to encapsulate the two ends and portions distal and proximal thereof.

Referring back to FIG. 2, the puller members 32 are generally parallel as they enter the control handle 16 at its distal end. In the embodiment illustrated, the control handle is configured such that the puller members 32 diverge as they approach the pulleys 52 of the steering mechanism 48, with a divider 80 facilitating this divergence. Regardless of its configuration, the molded member 60 connecting a respective puller wire 33 and tensile fiber 35 is situated between a pulley 52 and the distal end of the divider 80 (or at least sufficiently distal of the pulley 52) so that the puller wire 33 does not interact with the pulley and the molded member 60 does not interfere the deflection mechanism 48. In the illustrated embodiment of FIG. 2, the molded members 60 may be of any shape or volume so long as they can move freely in their designated pathways within the control handle 16.

Extending proximally from the molded member 60, the tensile fiber 35 is trained around a pulley 52. Each proximal end 65 of the tensile fiber continues to extend between a channel 84 defined by a pair of racks 86a and 86b and is connected to a free end of a spring 54 proximal the channel 84. In the illustrated embodiment, the springs are flat coil springs that exert a constant force to take up slack in the puller members 32 as they undergo cycles of distal and proximal movement with deflection operation of the catheter 10. In fact, if suitable, the springs can be connected or secured to the tensile fibers 35 by a molded member 60' in accordance with the foregoing embodiments and description of the molded member 60 with reference to FIGS. 3-6.

Figure 7:
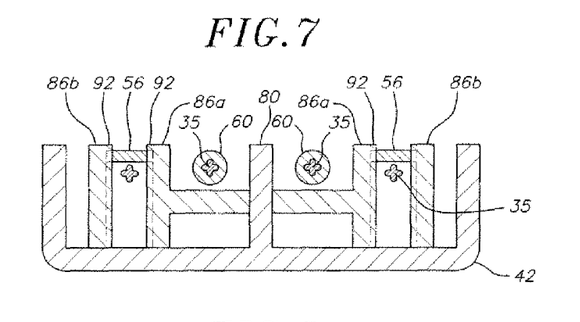
FIG. 7 is a longitudinal cross-sectional view of the control handle housing half of FIG. 2 taken along line 7-7.
Figure 8:
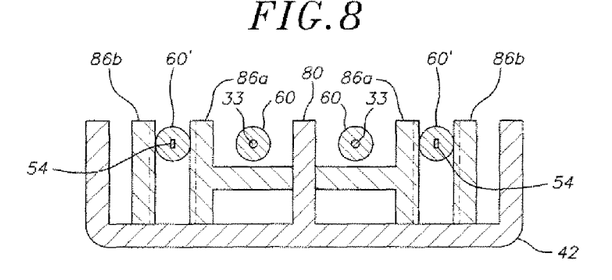
FIG. 8 is a longitudinal cross-sectional view of the control handle housing half of FIG. 2 taken along line 8-8.

The molded member 60' connecting the tensile fibers 35 and the springs 88 are situated between the respective pairs of racks 86a and 86b so that they can interact with stops 56. As better shown in FIGS. 7 and 8, the puller member (being the tensile fiber 35 in FIG. 7) passes between the racks 86a and 86b and under the stop 90, but the molded member 60 is formed with sufficient size or at least height (see FIG. 8) to encounter and abut with the stop (see FIG. 2). Thus, during assembly of the control handle 16 before the two halves 42 and of the housing are joined, the stops 56 are selectively positioned between the racks to achieve a desirable tension in each puller member. As means for adjusting tension setting of the puller members, the stops 56 and the racks 86a and 896b are configured for selective locking engagement at a selected position along the racks 86a and 896b. In the illustrated embodiment, the stops and the racks are each configured with notches 92 that engage with each other so the stops can interlock with the racks at a plurality of different positions along the racks. Once inserted between the racks, the stops are fixedly positioned to abut the proximal end of the molded members 60' and prevent their proximal movement beyond the distal end of the stops 90.

Figure 9:
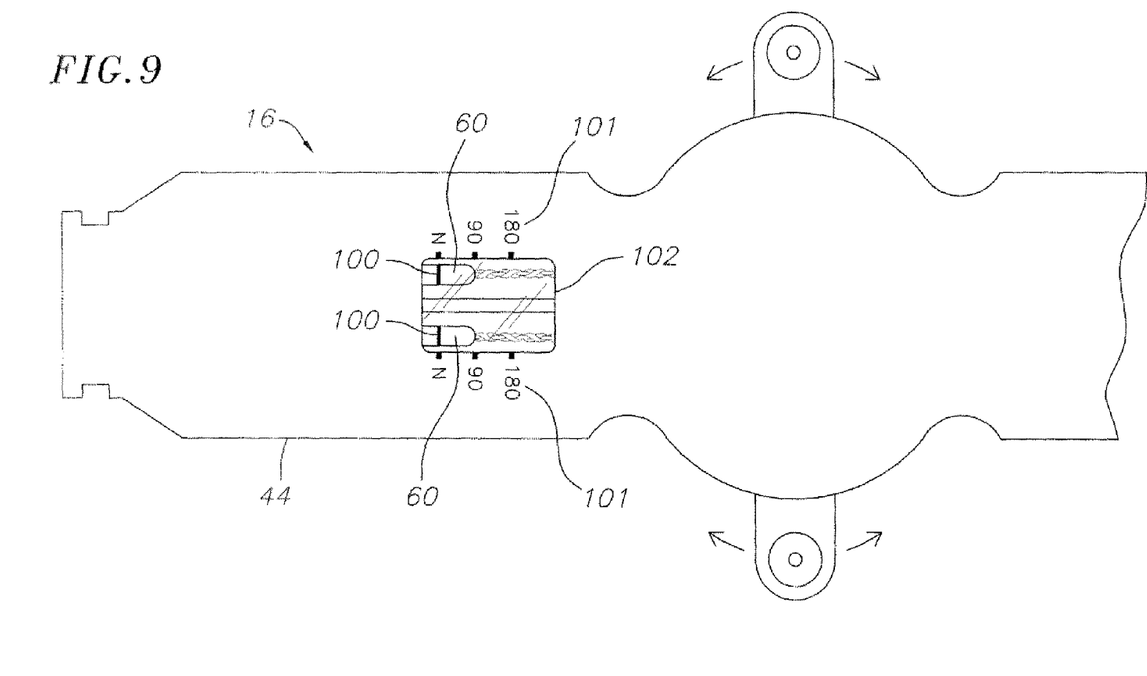
FIG. 9 is a top view of the control handle housing half of FIG. 2 assembled with the other control handle housing half.

As a further feature of the present invention, the molded members 60 between the puller wires 33 and tensile fibers 65 can be adapted to provide visual indication of the deflection and the degree of deflection of the catheter 10. With reference to FIGS. 2 and 9, the molded members 60 may comprise a marking or indicia 100 (e.g., a band) that is visible to an operator through a window 102 provided in the opposing half 44 after the control handle is assembled. An outer surface of the housing half 44 may also have marking or indicia 101, e.g., alphanumeric symbols indicating degree of deflection. Viewing the relative positions of the indicia 100 through the window 102, the operator can assess whether the catheter 10 is straight or deflected, the direction of deflection and/or degree of deflection. Moreover, the thermoplastic material of the molded members 60 may have glow in the dark properties, that is, by containing phosphors or other substances that radiate visible light, so that the molded members and/or markings are visible even in low light environment.

Figure 10:
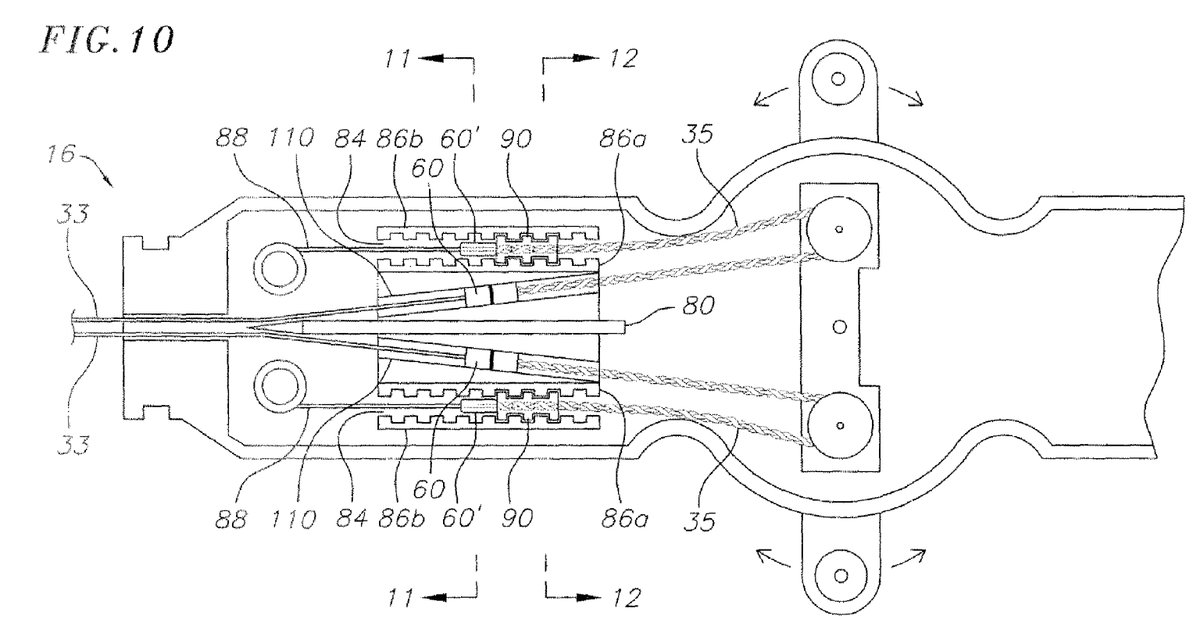
FIG. 10 is an alternative embodiment of a deflection assembly and control handle housing half.
Figure 11:
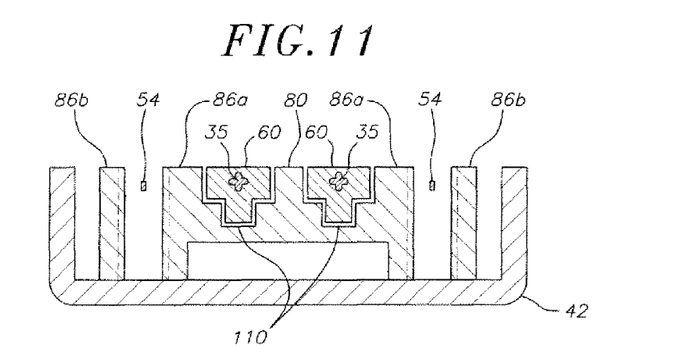
FIG. 11 is a longitudinal cross-sectional view of the control handle housing half of FIG. 10 taken along line 11-11.
Figure 12:
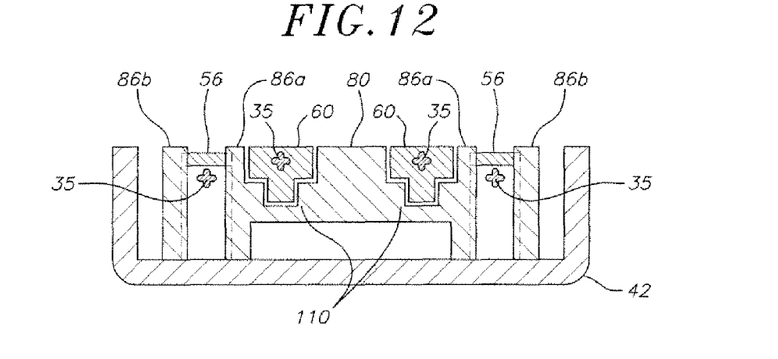
FIG. 12 is a longitudinal cross-sectional view of the control handle housing half of FIG. 10 taken along line 12-12.
Figure 13:
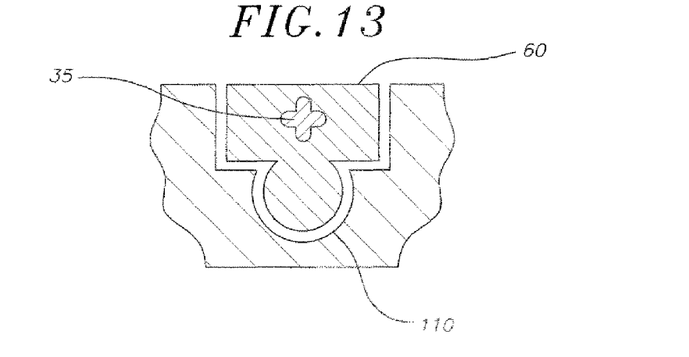
FIG. 13 is a detailed side cross-sectional view of an alternative embodiment of a track in locking engagement with a molded member.

In an alternative embodiment of the control handle as illustrated in FIGS. 10, 11 and 12, the molded members 60 are each configured to slide within tracks 110 formed between the divider 80 and each adjacent rack 86a in the housing half 42. The molded members 60 each have a T-shaped cross-section where a leg of the T-shape rides in the track. This embodiment may offer a smoother operation and a quieter deflection control handle. It is understood by one of ordinary skill in the art that the configuration of the tracks 110 and the molded members 60 may be varied as desired or appropriate. For example, an interlocking configuration as shown in FIG. 13 may be desired.

Figure 14:
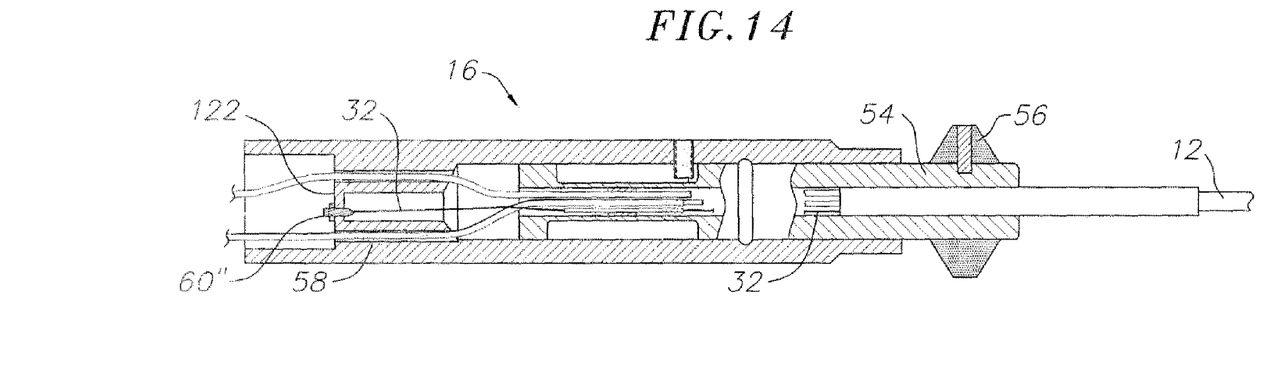
FIG. 14 is side cross-sectional view of an alternative embodiment of a catheter control handle.

Catheters may also be deflectable in a single direction as effectuated by a single puller member 32 whether it comprises a puller wire 33 for its entire length or has a proximal portion that is a tensile fiber 35. Such single deflection catheters may have a control handle 16, as shown in FIG. 14, that comprises a piston 54 with a thumb control 56 for manipulating the puller member 32. Such a control handle is described in U.S. Pat. No. 6,120,476, the entire disclosure of which is hereby incorporated by reference.

Figure 15:
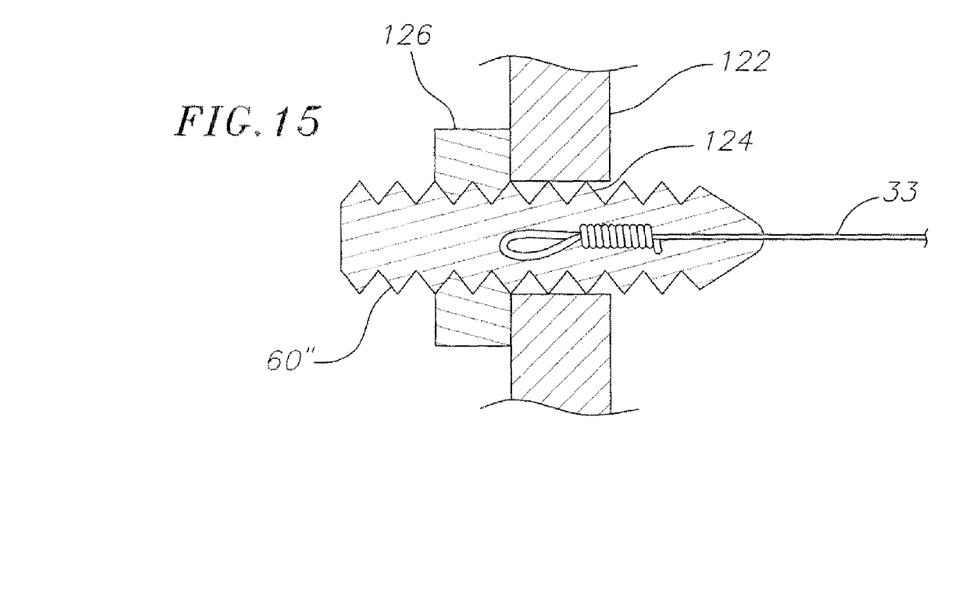
FIG. 15 is a cross-sectional view of a molded member securing a puller member to a transverse wall according to an alternate embodiment of the invention.

With reference to FIGS. 14 and 15, the puller member 32 extends through the piston 54 and its proximal end terminates at a distal end of a molded member 60" that serves to anchor or secure the proximal end of the puller member to a transverse wall 122 toward the proximal end of the control handle 16. In the illustrated embodiment, the molded member is configured as a screw that is inserted through hole 124 and fastened by a nut 126 that allows adjustment of the tension on the puller member 32 (which in the illustrated embodiment is a puller wire 33). In accordance with a feature of the present invention, the molded member 60" is of a similar construction as the aforementioned molded members 60 and 60' such that the preformed proximal end of the puller member is encased within a thermoplastic material. As such, the anchoring of a puller wire to a structure in the control handle is accomplished without significant deformations or changes in cross-sectional area of the puller wire that can cause earlier failure and breakage.

As used herein, insert molding refers to an injection molding process whereby plastic (including thermoplastic) is injected into a cavity and around an insert piece placed into the same cavity just prior to molding, thus the term insert molding. Here, the insert piece(s) are the preformed ends of a puller wire, a tensile fiber, a spring, or the like, that are encapsulated by the plastic.

Moreover, as used herein, thermoplastic material refers to materials that is plastic or deformable, melts to a liquid when heated and freezes to a crystalline or amorphous state when cooled sufficiently. Amorphous plastic polymer chain orientations are random and these types of plastics have high impact strengths and toughness. Crystalline plastic polymer chains are orderly, densely packed arrangements and these polymers in general have lower impact strengths and toughness. Most thermoplastics are high molecular weight polymers whose chains associate through weak van der Waals forces (polyethylene); stronger dipole-dipole interactions and hydrogen bonding (nylon); or even stacking of aromatic rings (polystyrene). Thermoplastic polymers differ from thermosetting polymers (Bakelite; vulcanized rubber) which once formed and cured, can never be remelted and remolded. Many thermoplastic materials are addition polymers; e.g., vinyl chain-growth polymers such as polyethylene and polypropylene.

Thermoplastics can go through melting/freezing cycles repeatedly and the fact that they can be reshaped upon reheating gives them their name. Thermoplastics as used herein include the following: Acrylonitrile butadiene styrene (ABS), Acrylic, Ethylene-Vinyl Acetate (EVA), Ethylene vinyl alcohol (EVAL), Fluoroplastics (PTFEs, including FEP, PFA, CTFE, ECTFE, ETFE), Ionomers, Liquid Crystal Polymer (LCP), Polyacetal (POM or Acetal), Polyacrylates (Acrylic), Polyacrylonitrile (PAN or Acrylonitrile), Polyamide (PA or Nylon), Polyamide-imide (PAI), Polyaryletherketone (PAEK or Ketone), Polybutadiene (PBD), Polybutylene (PB), Polybutylene terephthalate (PBT), Polyethylene terephthalate (PET), Polyurethane (TPU), Polycarbonate (PC), Polyketone (PK), Polyester, Polyethylene/Polythene/Polyethene, Polyetherimide (PEI), Polyethylenechlorinates (PEC), Polyimide (PI), Polylactic acid (PLA), Polymethylpentene (PMP), Polyphenylene oxide (PPO), Polyphenylene sulfide (PPS), Polyphthalamide (PPA), Polypropylene (PP), Polystyrene (PS), Polysulfone (PSU), Polyvinyl chloride (PVC), Spectralon, and combinations thereof.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A method of securing a puller member in a control handle for a deflectable catheter, comprising:
    preforming an end of the puller member;
    placing the preformed end in an insert mold;
    filling the insert mold with thermoplastic material to form a molded member; and
    positioning the molded member encasing the end of the puller member in a control handle.

2. A method of claim 1, further comprising shaping the thermoplastic material into a screw configuration.

3. A method of claim 2, further comprising fastening the molded member to a wall in the control handle.

4. A method of claim 1, further comprising:
    joining the end of the puller member with an end of a second puller member; and
    placing joined ends of the puller members in the insert mold.

5. A method of connecting two puller members of a deflectable catheter, comprising:
    joining ends of the puller members to form a joined connection;
    placing the joined connection in an insert mold; and
    fill the insert mold with thermoplastic material to form a molded member.

6. A method of claim 5, wherein the joined connection comprises:
    a loop formed in the end of one puller member; and
    a knot formed in the end of the other puller member.

7. A method of claim 6, wherein the one puller member is a puller wire and the other puller member is a high modulus fiber material.

8. A method of claim 5, wherein the joined connection comprises:
    a coil formed in the end of one puller member; and
    a knot formed in the end of the other puller member.

9. A method of claim 5, wherein the one puller member is a puller wire and the other puller member is a high modulus fiber material.

* * * * *